United States Patent [19]

Rose

[11] Patent Number: 4,715,387

[45] Date of Patent: Dec. 29, 1987

[54] AEROSOL FOR USE IN THE REDUCTION OF TOBACCO SMOKING

[75] Inventor: Jed E. Rose, Venice, Calif.

[73] Assignee: The Regents of the Univ. of California, Berkeley, Calif.

[21] Appl. No.: 768,966

[22] Filed: Aug. 23, 1985

[51] Int. Cl.⁴ .............................................. A24F 47/00
[52] U.S. Cl. .................................... 131/270; 131/273; 131/335; 131/337
[58] Field of Search ............... 131/337, 270, 271, 273, 131/335; 424/44, 28; 604/896, 897, 46, 289, 304

[56] References Cited

U.S. PATENT DOCUMENTS 4,635,651  1/1987  Jacobs .................................. 131/270

FOREIGN PATENT DOCUMENTS 1204018  9/1970  United Kingdom ................ 131/337
2133691  8/1984  United Kingdom ................ 131/271

Primary Examiner—V. Millin
Attorney, Agent, or Firm—Robert J. Schaap

[57] ABSTRACT

A method and an apparatus and composition used in the reduction of the incidence of tobacco smoking and which comprises an aerosol for application to the oral cavity and respiratory tract of an individual. The aerosol contains a food acid, such as citric acid, which is present in non-toxic amounts and capable of being inhaled. The aerosol may be in the form of a liquid spray or a finely divided solid. The droplets or particles contained in the aerosol are of proper size and have the food acid sufficient in content to simulate the sensations in the upper respiratory tract caused by tobacco smoke. In this way, the oral cavity sensations and the respiratory tract sensations simulate those created by tobacco smoke to replace the need for tobacco smoke. In another embodiment of the invention the food acid aerosol contains tobacco smoke of proper particle size so that the food acid particles migrate to the respiratory tract and the tobacco smoke remains in the oral cavity. In still a further embodiment of the invention, the aerosol contains small particles of a carrier such as a saccharide with tobacco smoke adsorbed thereon. In still another embodiment, the aerosol can be used in combination with a transdermal application of nicotine.

45 Claims, 7 Drawing Figures

AEROSOL FOR USE IN THE REDUCTION OF TOBACCO SMOKING

Government Rights

This invention was made with U.S. Government support under Grant No. 5 R01 DA02665-04 awarded by the Department of Health and Human Services and the Medical Research Service of the Veterans Administration. The Government has certain rights in this invention.

BACKGROUND OF THE INVENTION

1. Field of the Invention

This invention relates in general to certain new and useful improvements in an aerosol for use in the reduction of tobacco smoking, and more particularly to an aerosol which uses a food acid in non-toxic amounts, but sufficient in content and having proper particle size to simulate sensations in the respiratory tract which would normally be caused by tobacco smoke.

2. Brief Description of the Prior Art

In recent years, with the recognition of the harmful effects of tobacco smoking, there have been numerous campaigns and programs by governmental agencies and various health groups and other interested organizations to disseminate information about the adverse health effects resulting from tobacco smoking. Moreover, and as a result of this recognition of the harmful effects, there have been many programs directed to attempts in reducing smoking incidence.

The present successes in achieving reduction in the incidence of smoking have been relatively poor with presently known techniques. The present state of the art involves both behavioral approaches and pharmacological approaches. Approximately 80% or more of the tobacco smokers who initially quit smoking after using some behavioral or pharmacological approach to singly reduce smoking incidence, generally ralapse and return to the habit of smoking at their former rate of smoking within about a one year's period of time.

One of the most successful approaches to date in reducing the incidence of smoking relies upon nicotine containing chewing gum which is designed to reduce smoking withdrawal symptoms. The reported success rate, while still relatively low is approximately twice that of the other methods which have heretofore been employed. The use of the nicotine gum suffers from several problems including not only the bad taste and destruction of dental appliances, but the gastrointestinal upset which results therefrom and which also reduces compliance. In addition, it has been found that the nicotine containing gum does not satisfy the craving that most smokers experience for the distinct sensations in the throat and chest elicited by nicotine in the smoke. Over the course of many years of tobacco smoking, these particular sensations have become an important part of and associated with the habit of smokers and give rise to tobacco smoke dependency in most of the tobacco smokers.

The circulatory effects of nicotine aerosol inhalations have been studied as set forth in the Oct. 7, 1967 edition of the Lancet, pages 754–755. In this case, large doses of nicotine aerosols were applied to selected individuals in order to determine the effects on the individuals. Further, circadian blood nicotine concentrations have been studied as a result of cigarette smoking, as reported in Clinical Pharmacology and Therapeutics, December 1982, in an article by Neal L. Benowitz, M.D., pages 758–764.

A citric acid aerosol spray has been used for assessing the degree of airway anesthesia on the magnitude of added inspiratory load in the respiratory tract of individuals, as reported in "The Effects Of Airway Anesthesia on Magnitude Estimation of Added Inspiratory Resistive and Elastic Loads" by N. K. Burki et al, the American Review of Respiratory Diseases, 127, 2–4, 1983. In this case, the adequacy of airway anesthesia was assessed by absence of any cough in response to inhalation of a nebulized 20% solution of citric acid.

Heretofore, there has not been any attempt to use a food acid aerosol spray, as for example, a citric acid aerosol spray, in order to aid in the reduction of incidence of tobacco smoking.

OBJECTS OF THE INVENTION

It is, therefore, one of the primary objects of the present invention to provide a method of aiding in the reduction of the incidence of tobacco smoking by orally applying an aerosol containing a selected amount of a food acid which is capable of simulating the sensations in the respiratory tract normally caused by tobacco smoke.

It is another object of the present invention to provide a method of the type stated in which an aerosol is periodically applied to the oral cavity of an individual to thereby simulate the sensations in the oral cavity and in the respiratory tract caused by tobacco smoke and thereby replace the need for tobacco smoke by an individual.

It is a further object of the present invention to provide a food acid containing aerosol which has a selected particle size and also a selected amount of a food acid contained therein to simulate the conditions and sensations normally obtained by the inhalation of tobacco smoke.

It is also an object of the present invention to provide a method of aiding in the reduction of incidence of tobacco smoking by use of an aerosol which contains a combination of a food acid and tobacco smoke having a proper particle size.

It is another salient object of the present invention to provide an aerosol for inhalation to aid in smoking incidence reduction and where the aerosol contains a liquid carrier with a food acid therein present in non-toxic amounts and capable of simulating the sensations in the respiratory tract caused by nicotine in tobacco smoke.

With the above and other objects in view, my invention resides in the novel features of form, construction, arrangement and combination of steps and compositions and apparatus as hereinafter described.

BRIEF SUMMARY OF THE DISCLOSURE

This invention relates in broad aspect to a method of aiding in the reduction of incidence of tobacco smoking. In a preferred embodiment, the method utilizes an aerosol which relies upon application of the aerosol to the oral cavity and respiratory tract of an individual to correspond to the perceived need for tobacco smoke of that individual.

The method of the invention comprises administering an aerosol to the oral cavity of the individual where the aerosol contains particles of a food acid, such as citric acid, and which is present in non-toxic amounts and capable of being inhaled. The particles are of a proper size and have the food acid sufficient in content therein to simulate the sensations in the respiratory tract normally caused by tobacco smoke. In this way, the oral and respiratory tract sensations simulate those which would be created by tobacco smoke to thereby replace the need for tobacco smoke of an individual.

In one embodiment, the aerosol is a liquid spray which contains the food acid in a relatively inert liquid carrier and where the food acid is present in an amount of about 8% to about 35% by weight in the liquid carrier. More specifically, the liquid carrier is water and also, in one of the more preferred embodiments, the food acid is citric acid. In a more preferred embodiment, the food acid, such as citric acid, is present in the liquid carrier in an amount of about 15% by weight to about 25% by weight.

The food acid is preferably selected from the class consisting of citric acid, ascorbic acid, adipic acid, tartaric acid and mixtures of the foregoing.

The aerosol may adopt the form of a liquid aerosol so as to constitute an aerosol spray. However, the aerosol may be in the form of fine particles such as dust-sized particles. The term "particles" refers to either or both liquid or solid portions of the aerosol and the term "droplets" is often used to refer to the particles in liquid form.

The aerosol has particles in a proper size so as to migrate from the oral cavity into respiratory tract. Thus, and in a preferred embodiment, the aerosol has droplets of a size between 1 micron to about 15 microns in diameter. More preferably, the aerosol has droplets of a size ranging between about 5 microns to about 10 microns in diameter.

The present invention also relates to an aerosol composition which is used for inhalation by an individual to aid in smoking incidence reduction. The aerosol comprises the food acid mixed in that liquid carrier in the amount specified above and preferably containing particle sizes as mentioned above.

In another embodiment of the invention, it has been found that the food acid can be mixed with actual tobacco smoke so that the food acid can migrate to the respiratory tract and the tobacco smoke will generally remain in the oral cavity. In this way, many of the health problems which result from inhalation of tobacco smoke can be reduced, if not eliminated.

In this latter embodiment of the invention, the food acid is preferably present with particles having a first particle size within the range of about 1 to about 12 microns. The tobacco smoke is adsorbed on a particulate saccharide which has a second particle size, as for example, from about 12 microns to about 15 microns. In this way, the particle sizes are controlled such that the tobacco smoke will remain in the oral cavity and the food acid, such as citric acid, will migrate to the upper and lower respiratory tract.

In a further embodiment of the invention, it has been found that the aerosol can be comprised of saccharide particles which are finely divided and actual tobacco smoke adsorbed thereon. These particles are also sized so that they can migrate to the respiratory tract. In this way, many of the health problems which result from inhalation of large quantities of tobacco smoke can be reduced, if not eliminated.

In still another embodiment of the invention, it has been found to be effective to use the food acid aerosol of the present invention in combination with transdermally applied nicotine. The nicotine may be applied periodically by means of a patch placed on the users skin. In this way, nicotine levels can be increased in the blood to satisfy the perceived psychological demand for nicotine and the oral sensations normally obtained with tobacco smoke can be satisfied by the food acid aerosol of the present invention.

It has also been found to be effective to add an emulsifier, as for example, lecithin to the food acid aerosol spray of the invention to act as an emulsifier thereon. The use of the fatty acid emulsifier enables reduction of surface tension and thereby enables the production of droplets of smaller particle size.

This invention possesses many other advantages and has other purposes which will be made more clearly apparent from a consideration of the forms in which it may be embodied. They will now be described in detail for purposes of illustrating the general principles of the invention, but it is to be understood that such detailed descriptions are not to be taken in a limiting sense.

BRIEF DESCRIPTION OF THE DRAWINGS

Figure 1:
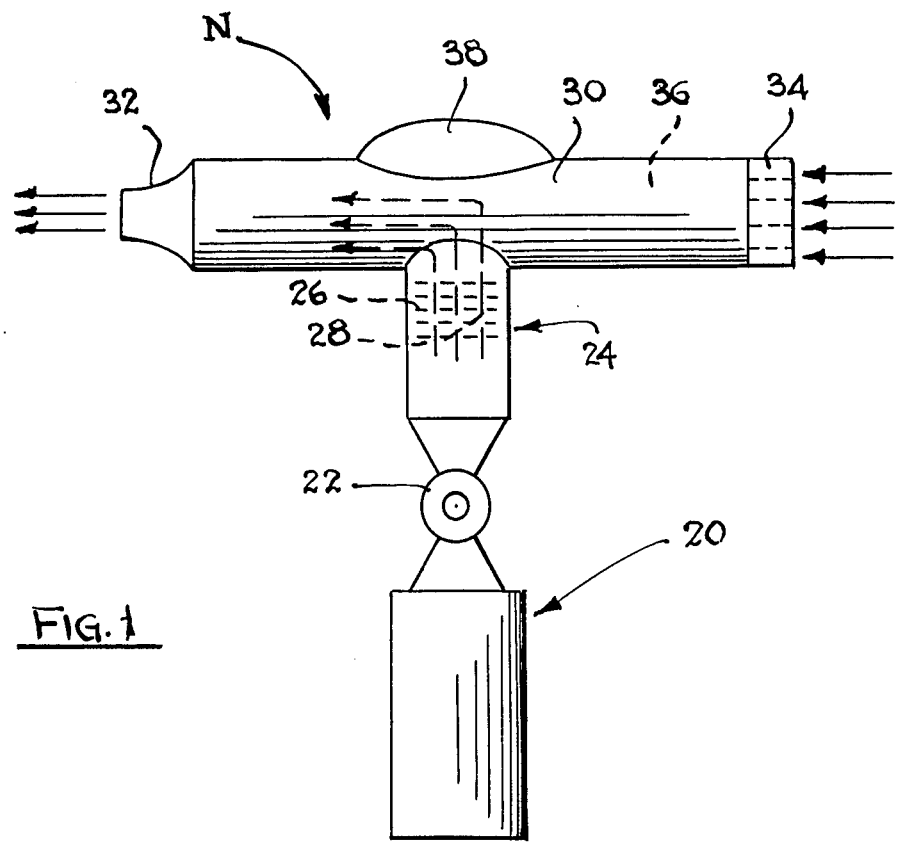
Figure 2:
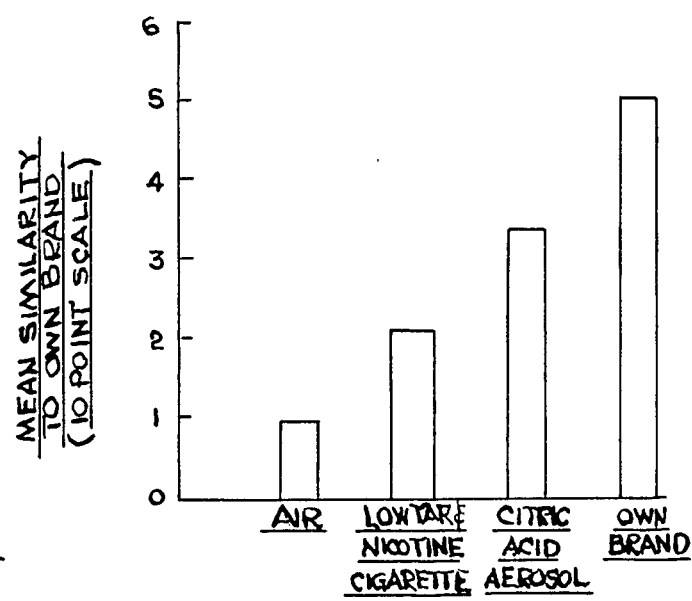
Figure 3:
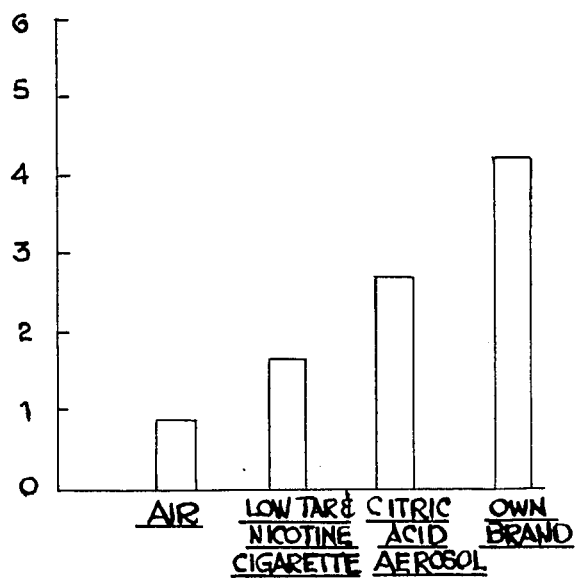
Figure 4:
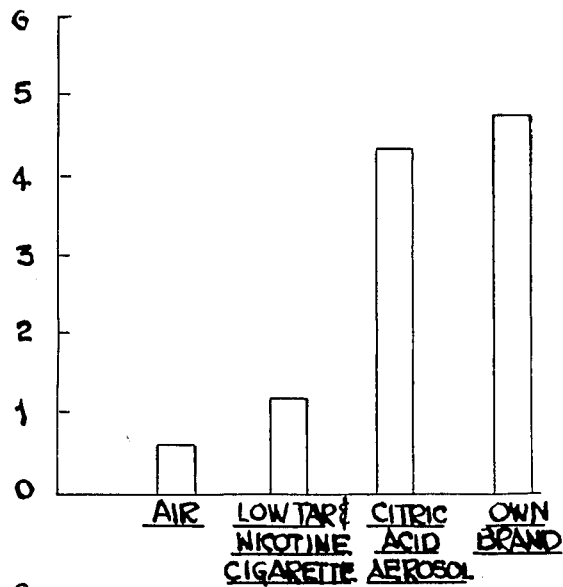
Figure 5:
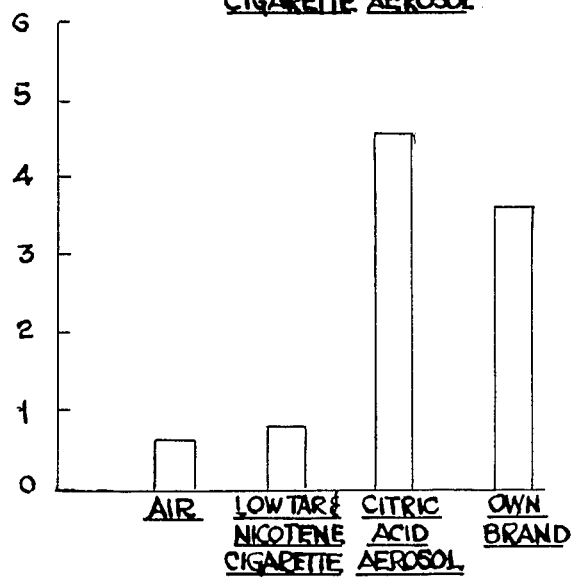
Figure 6:
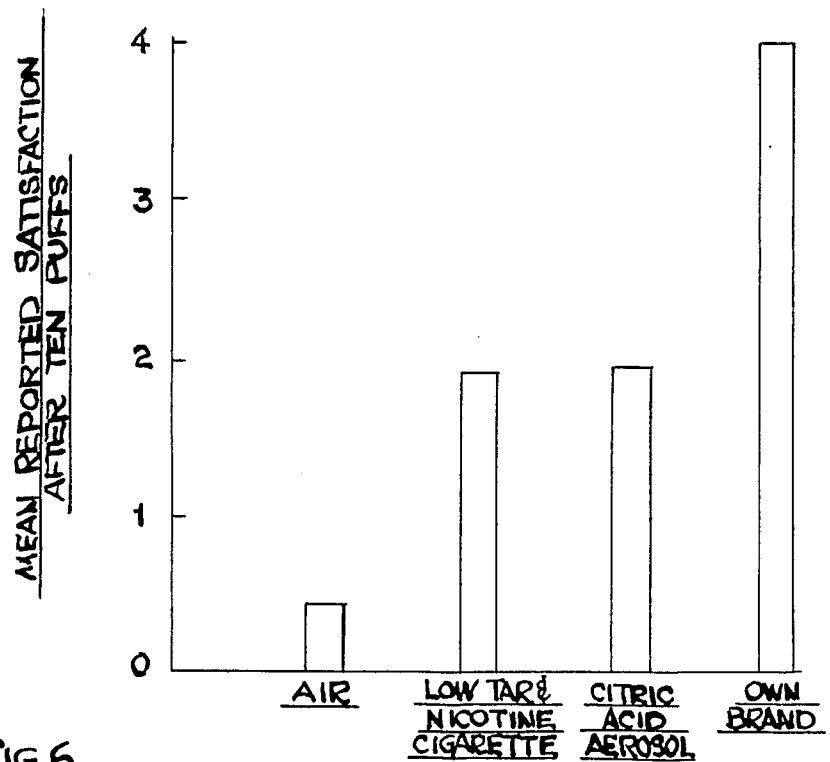
Figure 7:
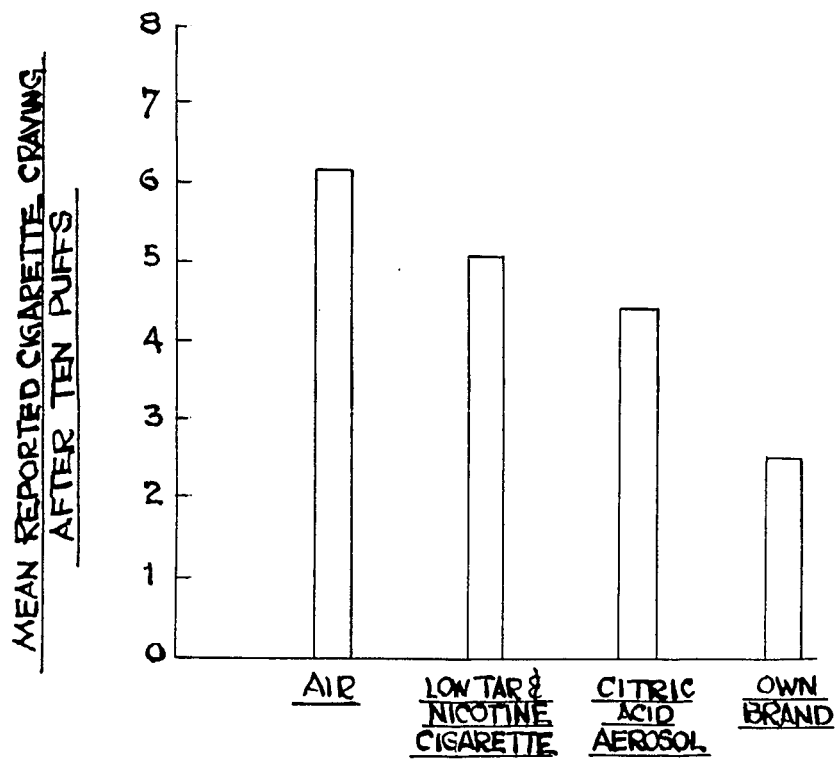

Having thus described the invention in general terms, reference will now be made to the accompanying drawings in which:

FIG. 1 is a schematic side elevational view of a nebulizer which may be used for the oral administration of the food acid containing aerosol;

FIG. 2 is a graph showing the mean similarity of a food acid aerosol of the present invention compared to a user's own brand, as well as a comparison to air inhalation and a low tar and nicotine cigarette;

FIG. 3 is a graph showing the mean liking (affection toward) a food acid aerosol of the present invention compared to a user's own preferred cigarette brand, as well as a comparison to air inhalation and a low tar and nicotine cigarette;

FIG. 4 is a graph showing the mean strength of a food acid aerosol of the present invention compared to the user's own preferred cigarette brand, as well as a comparison to air inhalation and a low tar and nicotine cigarette;

FIG. 5 is a graph showing the mean harshness of a food acid aerosol of the present invention comared to a user's own preferred cigarette brand, as well as a comparison to air inhalation and a low tar and nicotine cigarette;

FIG. 6 is a graph showing the reported satisfaction after several puffs of a food acid aerosol of the present invention compared to a user's own cigarette brand preference, as well as a comparison to air inhalation and a low tar and nicotine cigarette; and FIG. 7 is a graph showing the mean reported cigarette craving after several puffs of a food acid aerosol of the present invention compared to a user's own cigarette brand preference, as well as a comparison to air inhalation and a low tar and nicotine cigarette.

DETAILED DESCRIPTION OF PREFERRED EMBODIMENTS

The present invention provides an aerosol and a method of using a food acid containing aerosol. In a preferred embodiment, as hereinafter described, the aerosol is liquid based and is in the form of a spray which may be dispensed from a nebulizer N, as shown in FIG. 1. The nebulizer generally comprises a container such as a bottle 20 containing a solution of a food acid dissolved in a liquid carrier.

Located at the upper end of the container 20 is a valve 22, which may be in the form of a push-button valve or one with a rotatable valve core capable of being manually manipulated by a user, such that the food acid containing carrier can be dispensed from the container upon opening of the valve 22.

Located above the valve is a housing 24 having a plurality of internally located baffles 26. Each of these baffles 26 would have apertures 28 contained therein which control the size of the vehicle droplets. The upper end of the housing 24 is connected to and in fluid communication with an inhalation tube 30 which has a reduced end 32 for introduction into a user's mouth. The opposite end of the tube 30 may have a screen 34 over the open end thereof in order to strain and remove any foreign particles in an entering air stream.

The tube 30 has an internal chamber 36 which is designed to receive a charge of the aerosol spray. The tube 30 may also be provided with an enlarged hump 38 as shown in order to increase the overall size thereof and to insure that the content of the food acid containing liquid carrier (which may be in vapor form) within the tube is sufficient to constitute one full inhalation with a desired amount of the food acid.

The bottle 20 is preferably a pressurized bottle containing an inert gas under pressure. Various inert gases, such as Freon, or the like, which are normally found in containers of this type, may be employed.

The screen 34 may take the form of a resistive member which somewhat restricts the flow of air therethrough. In this way, the screen can act as a cigarette filter which creates a draw resistance, much in the same manner as one experiences when drawing air through a cigarette. For that matter, a conventional cigarette filter could be fitted upon the right-hand end of the tube 30.

The aerosol spray generally contains any food acid which is capable of being inhaled and which is capable of providing the sensations in the oral cavity and respiratory tract similar to those caused by nicotine in tobacco smoke. Thus, and for this purpose, the food acid must be present in the aerosol in an amount sufficient to simulate those sensations created by tobacco smoke, and thereby avoid the need of tobacco smoke to create such sensations. The food acid is present in a relatively minor amount in an inert liquid carrier and generally in an amount of 8% to about 35% by weight in the liquid carrier. More preferably, the food acid is present in an amount of about 15% to about 25% by weight in the liquid carrier.

The liquid carrier may be any of those liquid carriers normally employed in aerosol containers and in addition, the liquid carriers which are employed may be the same as those used for inhalers, as for example, inhalers in brochial dilators. It is important for the liquid carrier to be relatively inert so that it does not react with the body or with the food acid. One of the primary liquid carriers which may be employed is water. However, various low molecular weight alcohols such as ethanol, etc. could be used. In addition, glycerol, propylene glycol, etc. are effective carriers for the food acid.

One of the most preferred food acids which may be employed is citric acid since it creates sensations in the respiratory tract most closely approaching those created by normal tobacco smoke. However, essentially any food acid which is capable of being inhaled and which creates some sensation similar to that created by tobacco smoke, may be employed when it does not provide any unpleasantness or adverse side effects. For example, other food acids which have been found to be effective in the present invention include ascorbic acid, adipic, tartaric acid and mixtures of the foregoing.

As indicated previously, the food acid preferably is present in an amount of about 15% by weight to about 25% by weight, although it can range from about 8% by weight to about 35% by weight in the liquid carrier. The amount of the food acid will vary depending upon the overall effects desired and the particular food acid employed.

It is also possiblt to add one or more surfactants to the food acid containing liquid carrier in order to break up the droplets into smaller size. The lecithin and other surfactants are essentially a mixture of fatty acids which have been added to foods to act as emulsifiers or surfactants. These surfactants operate to split particles apart so as to reduce surface tension and thereby enable the generation of smaller particles. Lecithin is one excellent surfactant which can be used inasmuch as it is highly compatable with body tissue. Other surfactants which may be considered for use include sorbitan trioleate, cetylpyridinum, etc. When a surfactant is employed, it is preferably added in an amount of about 0.5% to about 1% by weight.

In normal tobacco smoke, approximately 0.1 milligrams of nicotine is obtained in each puff of a medium strength cigarette. This quantity of nicotine is known to satisfy the smoking and related tracheal sensations. However, by using the aerosol spray containing a food acid in the specified amounts and by controlling droplet sizes, as hereinafter described, it is possible to obtain the same effect. This is due to the fact that the size of the particles, such as the liquid droplets, determines the region of the respiratory tract to which the food acid would penetrate. For example, by using particles within a range from about 1 micron to about 5 microns, the food acid containing particles will penetrate to the lower respiratory regions for stimulation of those regions. Larger particles, e.g. droplets, as for example, 5 microns to about 10 microns would not penetrate very deeply in the respiratory tract and thus would stimulate the higher respiratory tract regions. Accordingly, by controlling the particle size, it is possible to stimulate that portion of the respiratory tract from which the smoker receives the greatest sensation.

In many cases, the tobacco smoker may desire to obtain some taste normally provided by cigarette smoke. While the citric acid and other food acids can simulate the respiratory tract sensations, they cannot necessarily simulate the taste provided by tobacco smoke. Accordingly, by incorporating a relatively small amount of tobacco smoke into the liquid carrier, it is therefore possible to provide both the stimulated sensations created by tobacco smoke as well as the taste created by tobacco smoke.

It is possible to incorporate tobacco smoke directly in the aerosol of the present invention. In many cases, the tobacco smoke does not effectively incorporate in the liquid carrier. Even when the tobacco smoke is dissolved in a liquid, it provides a rather unpalatable taste. Thus, for this purpose, the tobacco smoke can be captured on various solid particulate saccharides, such as starches. In this case, the tobacco smoke contacts the starch where it can effectively adhere to the surface of the starch. A jet of air directed against the starch thereafter generates a fine dust mixture of the starch containing the smoke particles. This is highly effective in that the smoke particles on the starch base will have a size up to about 15 microns which is sufficiently large so as to remain in the oral cavity and which also allows the smaller sized citric acid particles to migrate to the respiratory tract. In this case the citric acid is present in solid particulate form with a particle size generally not exceeding about 12 microns. It is also possible to use an aerosol containing the finely divided particulate starch with the tobacco smoke adsorbed thereon in absence of the food acid.

Some of the effective starches which can be used in accordance with the present invention are corn starch, lactose, which is generally a filler used in pharmaceutical products, flour, and other polysaccharides which are safe for inhalation.

In this latter embodiment of the invention, the aerosol composition will be a solid particulate matter composition. Thus, the nicotine particles on the starch base will be in admixture with solid food acid particles. However, since the particles are dust sized particles and are effectively fluidized, they can be nebulized and ejected from the nebulizer much in the same manner as a liquid spray.

As indicated previously, it is possible to control the area of the respiratory tract to which the food acid and the cigarette smoke will migrate by control of particle size. As an effective example, when using incorporated tobacco smoke, it is possible to produce a first mixture having particles within the range of about 1 micron to about 5 microns which contain the food acid. These particles will therefore penetrate to the lower respiratory regions. As a second mixture, it is possible to use a carrier for the cigarette smoke with smoke particles in the size of about 12 microns to about 15 microns. This portion of the aerosol would therefore remain in the oral cavity. The two components could therefore be mixed and introduced into the nebulizer. However, it is possible to use particle sizes within a range of about 1 micron to about 15 microns in accordance with the present invention.

In the event that the particles of food acid and the particles of starch tend to agglomerate, the food acid particles can be held in one compartment and the smoke containing starch particles can be held in another compartment. In this way the two sources of particles can be mixed when in a fluidized form as for example in a tube containing an air stream.

The amount of citric acid or other food acid can be varied in order to accommodate smokers who are accustomed to relatively mild tobacco smoke versus relatively strong tobacco smoke. Furthermore, the baffle system in the nebulizer can be adjusted to reduce the droplet size for penetration control. In addition, and as previously described, droplet size can be controlled by the addition of an emulsifier so that different sensations in different regions of the respiratory tract can be obtained.

The dis-association of the local tracheal stimulation produced by nicotine from its systemic physiological effects also is believed to allow for an effective extinction training procedure. Thus, the prior conditioning of the smoker in which smoke elicited throat stimuli were paired with the desired pharmacologic effects of nicotine in each puff can be reversed. The aerosol spray can be presented at different times of the day and may be employed in accordance with the smokers normal smoking pattern. Under normal conditioning theory, it is believed that the use of the food acid can hasten the extinction of the tracheal desire. A presentation of tracheal stimulation without an effective dose of nicotine reduces the association with the nicotine's desired effects.

It is also possible to use a transdermal application of nicotine to the individual in addition to the use of the aerosol in accordance with the present invention. For example, that transdermal patch described and claimed in co-pending U.S. patent application Ser. No. 727,525, filed Apr. 26, 1985 by Dr's. Jed E. Rose, et al, may be employed. In that case, the nicotine containing dermally applicable patch was applied to the skin of a user such that the nicotine in the patch was allowed to transdermally migrate into the blood stream of an individual at a rate sufficient to correspond to the nicotine level in the blood achieved by tobacco smoking. In this way, the nicotine can be introduced into the user's blood stream to satisfy the learned brain response to nicotine and the aerosol spray can be used to satisfy the oral and tracheal demands for nicotine without the otherwise harmful side effects of nicotine.

EXAMPLES

This invention is illustrated by, but not limited to the following examples.

EXAMPLE 1

An aerosol solution was prepared by mixing one hundred grams of citric acid in about seven hundred grams of water by weight in order to provide a 15% citric acid solution. This solution was thereupon introduced into a nebulizer having a lower container section and allowed to settle for about ten minutes. The nebulizer contained a Teflon tube of about one centimeter diameter and about two meters in length. An inlet of the Teflon tube had a cigarette filter attached to enable users to puff on the opposite end and feel a draw resistance comparable to that of a cigarette.

EXAMPLE 2

The citric acid aerosol solution of Example 1 in the nebulizer of Example 1 was used to test the acceptability of a citric acid aerosol in fifteen individual cigarette smokers. The smokers selected all smoked the equivalent of about a pack a day of cigarettes. Each of the smokers made blind ratings of the following types from puffing the following substances: (1) the citric acid aerosol mixture, (2) air, (3) a low tar and nicotine cigarette, which in this case was a Carlton filter hard pack cigarette, and (4) their own cigarette brand preference.

Each subject received four puffs of each of the above identified substances in random sequence. The aerosol was allowed to settle five to ten seconds before each inhalation in order to remove droplets larger than approximately ten microns. Puffs of smoke were delivered by drawing a volume of 35 cubic centimeters of smoke from the cigarettes with a syringe and injecting the smoke into the Teflon tube prior to inhalation.

To encourage subjects to focus on the tracheo-bronchial sensations associated with each test, and to minimize potential bias, each of the subjects were blindfolded. Further, the nostrils of each of the subjects were occluded with nose plugs and their mouths were numbed by rinsing with a topical anesthetic, which in this case was 2% lidocaine.

Each of the subjects rated their liking (pleasure associated) with each puff as well as the strength of the puff, the harshness and the similarity to their own customary brand of cigarette. The results of these tests are more fully illustrated in FIGS. 2–5 of the drawings. These results, generally indicate that the citric acid aerosol was rated significantly more similar to the subjects own preferred cigarette brands than air or another low tar and nicotine cigarette.

FIG. 2 illustrates that the mean similarity of the citric acid was rated significantly higher to the subjects own preferred cigarette brand than air which had a probability value (P) of less than 0.001 or the low tar and nicotine cigarette which had a probability value of less than 0.05. By reference to FIG. 3, it can be observed that the subjects tested liked the citric acid aerosol much better than air having a probability value of less than 0.01, or the low tar nicotine cigarette with a probability value of less than 0.05. By reference to FIG. 4, it can be observed that the citric acid aerosol was significantly stronger than air or the low tar nicotine cigarette. By reference to FIG. 5, it can be observed that the citric acid aerosol is significantly harsher than the air or comparable low tar and nicotine cigarette, with values comparable to the subjects own brand of cigarette.

Based on these tests, it was concluded that the citric acid aerosol simulated the tracheo-brochial sensations associated with cigarette smoking and provided an acceptable substitute for many, if not most of the tested cigarette smokers.

EXAMPLE 3

The same subjects used in Example 2 were provided with the citric acid aerosol prepared in accordance with Example 1 in order to determine whether the citric acid aerosol inhalations would diminish craving for cigarettes. In this case, each of the subjects were given a series of ten puffs of each of four substances which were (1) air, (2) the citric acid aerosol spray, (3) a low tar and nicotine cigarette and (4) the users customary preferred brand of cigarette. The same procedure was used, as reported in Example 2, to deliver the puffs of the substances to the subjects. Each of the subjects reported their craving and satisfaction after each set of puffs.

The means reported satisfaction of the subjects after ten puffs of the four substances showed that the citric acid aerosol was rated as significantly more satisfying than air with a probability value of less than 0.005 as shown in FIG. 6. The citric acid aerosol was also rated as reducing craving at a much greater rate than the air puffs, as shown in FIG. 7 with a probability value of less than 0.05.

Thus there has been described a unique and novel method and apparatus and composition which enables the effective reduction in the incidence of tobacco smoking and the attendant reduction, if not elimination, of dependency on tobacco smoking without relapse and return to the dependency. It should be understood that many changes, modifications, variations and other uses and applicaations will become apparent to those skilled in the art after considering this specification. Therefore, any and all such changes, modifications, variations and other uses and applications which may become apparent to those skilled in the art after considering this specification are deemed to be covered by the invention.

Having thus described my invention, what I desire to claim and secure by Letters Patent is:

1. A method of aiding in the reduction of incidence of tobacco smoking by simulating respiratory tract sensations approximating those obtained by inhalation of normal tobacco smoke, said method comprising administering an aerosol to the oral cavity of an individual and which aerosol contains particles of a food acid which is present in non-toxic amounts and capable of being inhaled, the particles being of a proper size and having the food acid sufficient in content to migrate to the respiratory tract and simulate the sensations in the respiratory tract caused by tobacco smoke, the size of the particles being established so that at least a moderately substantial portion of the particles remain in the upper respiratory tract, whereby the oral and respiratory tract sensations simulate those created by tobacco smoke to reduce the need of an individual for tobacco smoke.

2. The method of claim 1 further characterized in that said method comprises administering the aerosol spray which contains the food acid in water and where the food acid is present in an amount of about 8% to about 35% by weight in water.

3. The method of claim 1 further characterized in that the food acid is selected from the class consisting of citric acid, ascorbic acid, adipic acid, tartaric acid, and mixtures of the foregoing.

4. The method of claim 1 further characterized in that said method comprises varying the size of the particles to correspond to the portion of the respiratory tract where simulation is desired.

5. The method of claim 1 further characterized in that said aerosol has particles of a size ranging between 1 micron to about 15 microns in diameter.

6. The method of claim 1 further characterized in that said aerosol has particles of a size ranging between 5 microns to about 10 microns in diameter.

7. An aerosol spray for inhalation to aid in smoking incidence reduction, said spray comprising a liquid carrier with a food acid disolved therein, the food acid being present in a non-toxic amount which is capable of being inhaled and also present in an amount sufficient to simulate the sensations in the respiratory tract caused by tobacco smoke, the droplets of said spray having a proper size to migrate from the oral cavity to the respiratory tract to cause such sensations therein and thereby replace the need for tobacco smoke.

8. The aerosol spray of claim 7 further characterized in that the liquid carrier is water.

9. The aerosol spray of claim 7 further characterized in that the food acid is present in the liquid carrier in an amount of about 8% to about 35% by weight.

10. The aerosol spray of claim 7 further characterized in that the food acid is selected from the class consisting of citric acid, ascorbic acid, adipic acid, tartaric acid, and mixtures of the foregoing.

11. The aerosol spray of claim 7 further characterized in that the food acid is citric acid.

12. The aerosol spray of claim 7 further characterized in that the food acid is citric acid and is present in the liquid carrier, which is water, in an amount of about 15% to about 25% by weight.

13. The aerosol spray of claim 8 further characterized in that the droplets have a size ranging from about 1 micron to about 15 microns.

14. The aerosol spray of claim 8 further characterized in that the droplets have a size ranging from about 5 microns to about 10 microns.

15. The aerosol spray of claim 8 further characterized in that the spray is contained in and dispensed from a nebulizer as a fine mist.

16. The aerosol spray of claim 7 further characterized in that an emulsifier is incorporated into a liquid carrier with the food acid dissolved therein to reduce surface tension and control particle size.

17. The aerosol spray of claim 16 further characterized in that the emulsifier is lecithin.

18. A method of aiding in the reduction of incidence of tobacco smoking, said method comprising administering an aerosol to the oral cavity of an individual which contains a nebulized food acid capable of being inhaled and of a first particle size and particles of a second particle size containing tobacco smoke, so that the food acid particle size is selected to migrate to the respiratory tract and the tobacco smoke containing particles will generally remain in the oral cavity.

19. The method of claim 18 further characterized in that the food acid particles are of a smaller size than the tobacco smoke containing particles.

20. The method of claim 18 further characterized in that the food acid is selected from the class consisting of citric acid, ascorbic acid, adipic acid, tartaric acid, and mixtures of the foregoing.

21. The method of claim 18 further characterized in that the food acid is citric acid.

22. The method of claim 19 further characterized in that said method comprises administering an aerosol spray which contains a mixture of the food acid and tobacco smoke in a relatively inert liquid carrier and where the food acid is present in an amount of about 9% to about 35% by weight in the liquid carrier.

23. The method of claim 19 further characterized in that said method comprises administering an aerosol spray which contains a mixture of the food acid in water and tobacco smoke in a liquid carrier which is water and where the food acid is present in an amount of about 9% to about 35% by weight in the water.

24. The method of claim 23 further charcterized in that said method comprises administering an aerosol spray which contains a mixture of the food acid and tobacco smoke in water and where the food acid is citric acid present in an amount of about 15% to about 25% by weight in the water.

25. The method of claim 19 further characterized in that said method comprises administering an aerosol which contains a mixture of the food acid in a solid particulate form and particles containing tobacco smoke in solid particulate form and which mixture is sufficiently fluidized so as to be nebulized similar to that of a liquid spray.

26. The method of claim 23 further characterized in that the mixture comprises an emulsifier therein.

27. An aerosol for inhalation to aid in smoking incidence reduction, said aerosol containing particles of a food acid present in non-toxic amounts and having a first particle size and particles with tobacco smoke thereon in combination therewith and having a second particle size so that the food acid particles migrate to the respiratory tract and where the tobacco smoke containing particles will generally remain in the oral cavity.

28. The aerosol of claim 27 further characterized in the particles are in a mixture in a liquid carrier.

29. The aerosol of claim 28 further characterized in that the liquid carrier is water.

30. The aerosol of claim 25 further characterized in that the tobacco particles comprise a saccharide base and the tobacco particles and food acid are a solid mixture.

31. The aerosol of claim 25 further characterized in that the tobacco particles comprise a starch base and the tobacco particles and food acid are a solid mixture.

32. The aerosol of claim 27 further characterized in that the food acid is citric acid.

33. The aerosol of claim 27 further characterized in that the food acid particles have a size ranging from about 1 micron to about 12 microns.

34. The aerosol of claim 27 further characterized in that the food acid particles have a size ranging from about 5 microns to about 10 microns.

35. A method of aiding in the reduction of incidence of tobacco smoking, said method comprising administering an aerosol which contains a nebulized food acid capable of being inhaled to the oral cavity of an individual, and transdermally applying nicotine to an individual having the aerosol administered thereto so that the nicotine can satisfy a nicotine demand in the blood stream thereof.

36. The method of claim 35 further characterized in that the aerosol has a particle size sufficient so that the particles of the aerosol will migrate to the respiratory tract of the user.

37. The method of claim 35 further characterized in that the food acid is selected from the class consisting of citric acid, ascorbic acid, adipic acid, tartic acid and mixtures of the foregoing.

38. The method of claim 37 further characterized in that the food acid is citric acid.

39. The method of claim 35 further characterized in that the nicotine is transdermally applied to the individual by a transdermal patch located on the skin of the user.

40. A method of aiding in the reduction of incidence of tobacco smoking, said method comprising generating an aerosol which contains saccharide particles, with tobacco smoke adsorbed on the surface thereof, administering the aerosol thus generated to the oral cavity of an individual and with the particles having a particle size so that the tobacco smoke adsorbed saccharide will migrate to the respiratory tract.

41. The method of claim 40 further characterized in that the particles are a starch.

42. A method of aiding in the reduction of incidence of tobacco smoking, said method comprising administering an aerosol in a spray form to the oral cavity of an individual and which aerosol contains particles of a food acid incorporated in a relatively inert liquid carrier, said food acid being present in an amount of about 8% to about 35% by weight in the liquid carrier and in which said food acid is present in said aerosol in non-toxic amounts and capable of being inhaled, the particles being of a proper size and having the food acid sufficient in content to migrate to the respiratory tract and simulate the sensations in the respiratory tract caused by tobacco smoke, whereby the oral and respiratory tract sensations simulate those created by tobacco smoke to reduce the need of tobacco smoking by an individual.

43. The method of claim 42 further characterized in that the liquid carrier is water.

44. The method of claim 42 further characterized in that the food acid is citric acid.

45. A method of aiding in the reduction of incidence of tobacco smoking, said method comprising administering an aerosol spray to the oral cavity of an individual and which aerosol contains particles of a citric acid contained in water and in non-toxic amounts and capable of being inhaled, the citric acid being present in an amount of about 15% to about 25% by weight in the water, the particles being of a proper size and having the food acid sufficient in content to migrate to the respiratory tract and simulate the sensations in the respiratory tract caused by tobacco smoke, whereby the oral and respiratory tract sensations simulate those created by tobacco smoke to reduce the need of tobacco smoking by an individual.

* * * * *